US009661987B2

(12) United States Patent
Weitzner et al.

(10) Patent No.: US 9,661,987 B2
(45) Date of Patent: May 30, 2017

(54) DISPOSABLE SHEATH (75) Inventors: Barry Weitzner, Acton, MA (US);
Paul Smith, Smithfield, RI (US);
Robert B. DeVries, Northborough, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 274 days.

(21) Appl. No.: 13/489,885

(22) Filed: Jun. 6, 2012

(65) Prior Publication Data

US 2012/0316391 A1    Dec. 13, 2012

Related U.S. Application Data

(60) Provisional application No. 61/494,193, filed on Jun. 7, 2011.

(51) Int. Cl.
| | | |
|---|---|---|
| A61B 1/04 | (2006.01) | |
| A61B 1/00 | (2006.01) | |
| A61B 1/018 | (2006.01) | |
| A61B 17/00 | (2006.01) | |
| A61B 17/29 | (2006.01) | |

(52) U.S. Cl.
CPC ...... *A61B 1/00135* (2013.01); *A61B 1/00142* (2013.01); *A61B 1/018* (2013.01); *A61B 17/00234* (2013.01); *A61B 1/00154* (2013.01); *A61B 2017/0023* (2013.01); *A61B 2017/00477* (2013.01); *A61B 2017/2906* (2013.01)

(58) Field of Classification Search
CPC ............ A61B 1/00135; A61B 1/00142; A61B 1/0008; A61B 1/00089; A61B 1/018; A61B 1/00154

USPC ........ 600/119, 121, 139, 153, 104, 114, 129
See application file for complete search history.

(56) References Cited

U.S. PATENT DOCUMENTS

| | | | |
|---|---|---|---|
| 5,370,659 A | 12/1994 | Sakashita | |
| 5,630,782 A | 5/1997 | Adair | |
| 5,817,015 A | 10/1998 | Adair | |
| 6,120,434 A * | 9/2000 | Kimura et al. | 600/114 |
| 6,352,503 B1 * | 3/2002 | Matsui | A61B 1/00071 |
| | | | 600/104 |
| 6,951,568 B1 * | 10/2005 | Chin | 606/190 |

(Continued)

FOREIGN PATENT DOCUMENTS

| | | |
|---|---|---|
| JP | H 067366 | 1/1994 |
| JP | 2003144377 | 5/2003 |

(Continued)

OTHER PUBLICATIONS

International Search Report for International Patent Application No. PCT/US2012/052195 dated Nov. 29, 2012, 5 pages.

(Continued)

*Primary Examiner* — Timothy J Neal
(74) *Attorney, Agent, or Firm* — Bookoff McAndrews, PLLC (57) ABSTRACT

A sheath for a medical instrument may include an elongate body extending from a proximal end to a distal face, and a first hollow lumen extending from a first end proximate the proximal end to a second end proximate the distal face. The sheath may also include a transparent window positioned at the second end of the first lumen to seal the first lumen at the second end. The transparent window may be configured to transmit light therethrough.

20 Claims, 9 Drawing Sheets

(56) References Cited

U.S. PATENT DOCUMENTS

| | | |
|---|---|---|
| 2002/0072652 A1 | 6/2002 | Berci et al. |
| 2003/0130564 A1* | 7/2003 | Martone et al. .............. 600/121 |
| 2004/0111009 A1 | 6/2004 | Adams et al. |
| 2005/0090709 A1 | 4/2005 | Okada et al. |
| 2005/0222581 A1 | 10/2005 | Fischer, Jr. et al. |
| 2005/0272977 A1* | 12/2005 | Saadat et al. ................. 600/114 |
| 2006/0189845 A1 | 8/2006 | Maahs et al. |
| 2006/0235356 A1 | 10/2006 | Yamaya |
| 2007/0142709 A1 | 6/2007 | Martone et al. |
| 2007/0270646 A1 | 11/2007 | Weiner |
| 2008/0188869 A1* | 8/2008 | Weitzner et al. ............. 606/130 |
| 2008/0193631 A1* | 8/2008 | Kanamori et al. ............. 427/2.1 |
| 2008/0221391 A1 | 9/2008 | Weitzner et al. |
| 2008/0243176 A1 | 10/2008 | Weitzner et al. |
| 2008/0249362 A1* | 10/2008 | Jiang et al. ................... 600/121 |
| 2009/0036739 A1 | 2/2009 | Hadani |
| 2010/0056863 A1 | 3/2010 | Dejima et al. |
| 2010/0063358 A1* | 3/2010 | Kessler ........................ 600/121 |
| 2010/0298642 A1 | 11/2010 | Trusty et al. |
| 2011/0046442 A1 | 2/2011 | Matsushita |
| 2011/0118543 A1* | 5/2011 | Dosher .............. A61B 17/3421 600/104 |
| 2011/0201889 A1 | 8/2011 | Vayser et al. |
| 2013/0053644 A1 | 2/2013 | Smith et al. |
| 2013/0053645 A1 | 2/2013 | Weitzner et al. |

FOREIGN PATENT DOCUMENTS

| | | |
|---|---|---|
| JP | 2004195037 | 7/2004 |
| JP | 2005177080 | 7/2005 |
| JP | 2010057914 | 3/2010 |
| WO | WO 2010/111461 | 9/2010 |

OTHER PUBLICATIONS

International Preliminary Report on Patentability and Written Opinion issued in PCT International Application No. PCT/US2012/052195 mailed Mar. 13, 2014, 9 pages.

International Search Report and Written Opinion from PCT/US2012/052194, mailed Mar. 13, 2014, 9 pages.

* cited by examiner

DISPOSABLE SHEATH

CROSS-REFERENCE TO RELATED APPLICATIONS

This application is based upon and claims the benefit of priority under 35 U.S.C. §119(e) of U.S. Provisional Application No. 61/494,193 to Weitzner et al. filed on Jun. 7, 2011, the complete disclosure of which is incorporated by reference herein.

FIELD OF THE INVENTION

Embodiments of the present invention relate to a disposable sheath for a reusable medical device. In particular, exemplary embodiments of the present invention relate to disposable sheaths that allow reusable medical devices to be used within the body of a patient without direct tissue contact.

BACKGROUND OF THE INVENTION

Medical devices such as endoscopes and other similar medical instruments may be used for diagnostic and therapeutic applications within the body of a patient. While some of these instruments are disposable instruments that are discarded after a single use, others may be reusable. These reusable instruments have to be sterilized between uses to prevent cross contamination between patients. To reduce issues associated with sterilization and contamination, some of these reusable devices may be covered with sterile disposable sheaths during use. Such sheaths may be elongated, tubular components having a lumen for the insertion of the reusable medical device. During use, the sheath may isolate the reusable instrument from body tissue. After use, the disposable sheath is removed from the instrument and discarded. Since the reusable instruments themselves are not in contact with body tissue, the likelihood of contamination is minimized.

In some cases, it may be desirable to direct multiple medical instruments into the body to assist in a medical application. Some of these instruments may be disposable while others may be fully or partially reusable. Introducing these multiple instruments into the body individually may be inefficient and may also increase patient discomfort and trauma. To minimize patient discomfort and improve the efficacy of the medical procedure, it may be advantageous to direct these multiple instruments into the body through the same disposable sheath. In these cases, it may be desirable to isolate the reusable instruments from the disposable instruments to minimize contamination. Embodiments of the current disclosure are directed to disposable sheaths that enable multiple medical instruments to be used alongside each other within the body.

SUMMARY OF THE INVENTION

An embodiment of the invention discloses a sheath for a medical instrument. The sheath may include an elongate body extending from a proximal end to a distal face and a first hollow lumen extending from a first end proximate the proximal end to a second end proximate the distal face. The sheath may also include a transparent window positioned at the second end of the first lumen to seal the first lumen at the second end. The transparent window may be configured to transmit light therethrough.

Various embodiments of the invention may include one or more of the following aspects: a second lumen may extend from the proximal end to the distal face, the second lumen may be open at the distal face; a sealing device may be coupled to the second lumen proximate the proximal end and configured to seal around a medical instrument inserted through the sealing device; a third lumen may extend from the proximal end to the distal face, the third lumen may be open at the distal face; the elongate body may include a diverging element positioned proximate the distal face, wherein activation of the diverging element may enable the distal ends of the second lumen and the third lumen to diverge from each other; the first lumen may be open at the first end; the sheath may include a neck region that extends from the distal face to the second end, at least a portion of the first lumen may be positioned in the neck region; the neck region may be configured to deflect relative to the distal face of the elongate body; the sheath may further include a port that extends from a location proximate the proximal end to the first end, at least a portion of the first lumen may be positioned in the port, wherein the port may be angled relative to a longitudinal axis of the sheath; and the transparent window may seal the first lumen such that entry of biological fluids into the first lumen at the second end is substantially prevented.

An embodiment of the invention discloses a medical device including a flexible sheath extending from a proximal end to a distal face. The device may include a first hollow lumen extending through the disposable sheath from the proximal end to the distal face and a neck region that extends the first lumen from the distal face of the sheath to a second end that is distal to the distal face of the sheath. The first lumen may be closed at the second end by a transparent window. The device may also include a second lumen and a third lumen each extending from the proximal end to the distal face of the sheath. The second and the third lumens may be open at the distal face.

Various embodiments of the invention may include one or more of the following aspects: a first sealing device coupled proximate the proximate end of the second lumen, the first sealing device may be configured to seal around a medical instrument inserted therethrough; the sheath may include a diverging element positioned proximate the distal face, wherein activation of the diverging element may enable the distal face of the second lumen and the third lumen to diverge from each other; an end effector that extends from the distal face of the sheath through the second lumen, the end effector may be coupled to an elongate member that extends through the second lumen to a third end between the distal face and the proximal end, the third end of the elongate member may include an interface member that is configured to operably couple with a first instrument inserted through the proximal end of the second lumen; a second instrument removably positioned in the first lumen, the second instrument may include an elongate body extending along a length of the disposable sheath and including an optical device positioned proximate the transparent window; a third medical instrument that includes an end effector extending from the sheath at the distal face.

An embodiment of the invention may disclose a method of using a medical device. The method may include inserting a distal end of a sheath into the body of a patient. The sheath may include an elongate body extending from a proximal end to the distal end and a first lumen extending therethrough, the first lumen may be closed at the distal end by a transparent window. The method may also include inserting a first medical instrument having an optical device into the first lumen of the sheath either before, during, or after the sheath is inserted into the body. The method may further include positioning the optical device of the first medical instrument proximate the transparent window.

Various embodiments of the method may include one or more of the following aspects: inserting a second medical instrument through a second lumen of the sheath to extend an end effector of the second medical instrument out of the distal end of the sheath; activating the optical device of the first medical instrument to transmit light through the transparent window; and activating an articulation feature of the first medical instrument to move at least a section of the elongate body of the sheath.

An embodiment of the invention may disclose a medical device. The medical device may include a sheath extending from a first end to a second end with a lumen extending longitudinally therethrough. The medical device may also include an interface member positioned between the first end and the second end to separate the lumen into a fluidly decoupled distal portion and a proximal portion. The medical device may also include an end effector positioned in the distal portion of the lumen and extending through the second end of the lumen, a proximal end of the end effector being coupled to the interface member. The medical device may further include an elongate member positioned in the proximal portion of the lumen and extending through the proximal end of the lumen. A distal end of the elongate member may be coupled to the interface member and may be adapted to activate the end effector.

BRIEF DESCRIPTION OF THE DRAWINGS

The accompanying drawings, which are incorporated in and constitute a part of this specification, illustrate embodiments of the invention and together with the description, serve to explain the principles of the invention.

DESCRIPTION OF THE EMBODIMENTS

Reference will now be made to exemplary embodiments of the invention, examples of which are illustrated in the accompanying drawings. Wherever possible, the same reference numbers will be used throughout the drawings to refer to the same or like parts. The terms "proximal" and "distal" are used herein to refer to the relative positions of a device. As used herein, "proximal" refers to a position relatively closer to the exterior of the body or closer to a user (such as, a physician, surgeon, etc.) of the device. In contrast, "distal" refers to a position relatively further away from the user of the device or closer to the interior of the body.

Figure 1A:
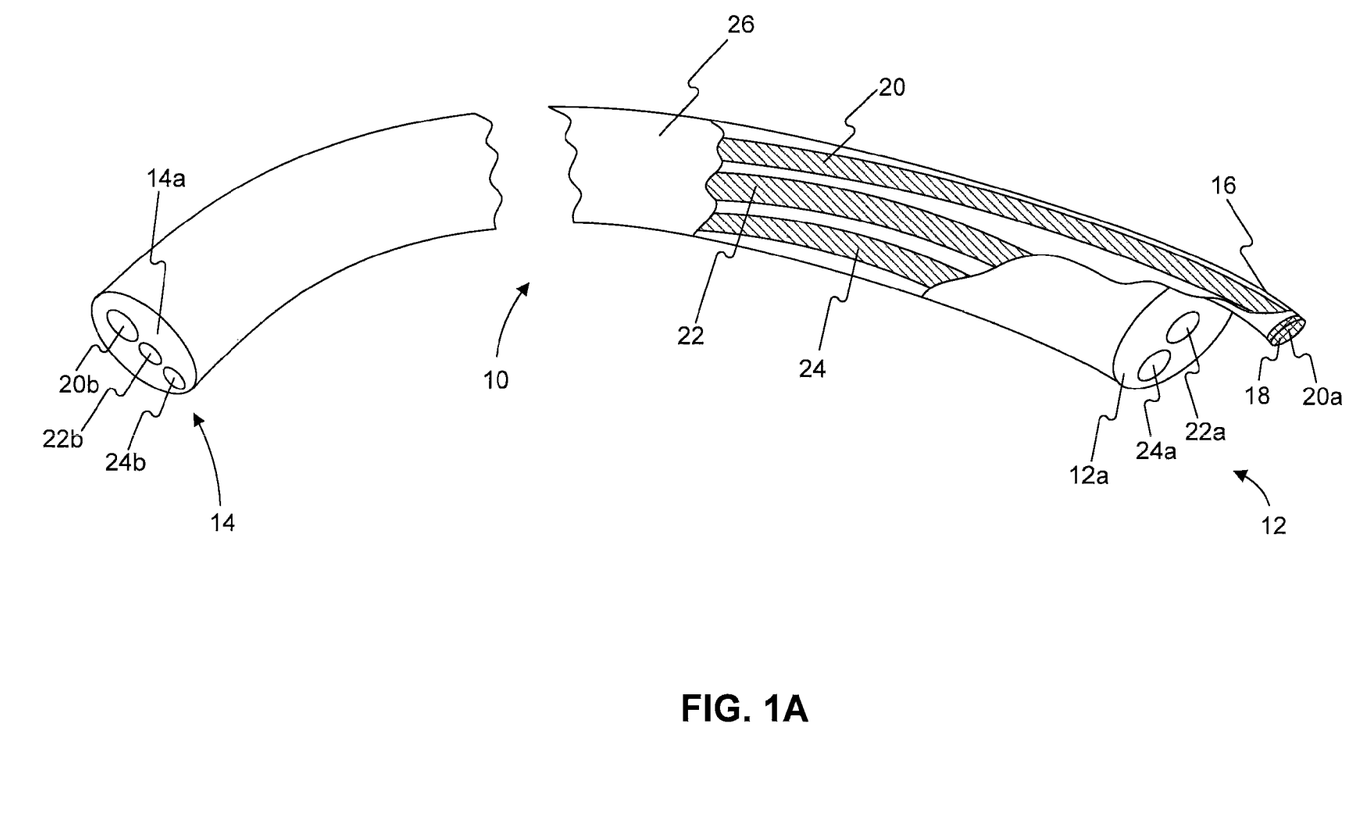
FIG. 1A is a schematic view of an exemplary embodiment of a sheath of the current disclosure.

FIG. 1A depicts an exemplary guide or sheath 10 of the current disclosure. Sheath 10 may include a flexible elongate body 26 that extends between a proximal end 14 and a distal end 12. During application, the distal end 12 may be positioned within the body of a patient while the proximal end 14 may extend outside the body. In some embodiments, the proximal end 14 of sheath 10 may include a proximal attachment (not shown). The distal end 12 of the sheath 10 may be inserted into the body of the patient and pushed into the body (such as, for example, through a body tract) to position the distal end 12 at a desired work site within the body. The sheath 10 may be inserted into the body transluminally, intraluminally, percutaneously or by any other means. For example, the distal end 12 of sheath 10 may be inserted into the body of a patient through the mouth and pushed into the body through the esophagus to position the distal end 12 proximate the stomach wall, while the proximal end 14 is positioned outside the body. Elongate body 26 may be flexible so as to enable the sheath 10 to bend and pass through tortuous body tracts as the distal end 12 advances into the body through the body tract. In some embodiments, an external surface of elongate body 26 may be made of, or coated with, a polymeric or a lubricious material (such as, for example, MDX coating, PTFE extrusions, etc.) to enable the sheath 10 to pass through body cavities with ease. In some embodiments, the external surface of elongate body 26 may include features such as, for example, bumps, ribs, etc. to reduce surface contact and friction.

One or more lumens (such as, for example, first lumen 20, second lumen 22, and third lumen 24) may extend through the elongate body 26 from the proximal end 14 to the distal end 12. While one or more of these lumens may be sealed at the distal end 12 to prevent the entry of biological fluids thereinto, the other lumens may be open. For instance, first lumen 20 may be sealed at the distal end 12 as illustrated in FIG. 1A. An optically transparent window (such, as for example, a viewing lens 18) may be provided at the distal end 12 of first lumen 20 to allow light to pass therethrough, while isolating the interior of first lumen 20 from body tissue and fluids. Any type of material that allows at least a portion of light to pass therethrough may be used as viewing lens 18. In some embodiments, viewing lens 18 may include a plain glass window, a light filter, a magnifying glass, etc. During application, a reusable medical instrument (such as, for example, the reusable instrument 50 discussed with reference to FIGS. 3A and 3B) may be directed into the body through first lumen 20. This reusable instrument may be inserted into the first lumen 20 through an opening 20b at the proximal end 14 of the sheath 10. The reusable instrument may then be pushed into the body through the first lumen 20 to position its distal end proximal to the viewing lens 18. In some embodiments, as illustrated in FIG. 1A, at the distal end 12, the first lumen 20 may include a protruding neck region 16 that extends past a distal face 12a of the sheath 10. In these embodiments, the distal-most end 20a of the first lumen 20 may be longitudinally displaced from the distal face 12a, and viewing lens 18 may be provided at the distal-most end 20a.

As opposed to the first lumen 20 which is sealed at the distal end 12 and open at the proximal end 14, the second lumen 22 and the third lumen 24 may be open at both the proximal end 14 and the distal end 12. A medical instrument or device may be inserted into the second and the third lumens 22, 24 through openings 22b, 24b at the proximal end 14. These instruments may then be pushed into the sheath 10 to extend the distal ends of the instruments into the body through openings 22a, 24a at the distal end 12 of sheath 10. The second lumen 22 and the third lumen 24 may provide access for medical instruments that may aid in performing any desired medical procedure within the body.

Sheath 10 may be made of any material (metal, plastic, polymeric, etc.) and have any stiffness (of flexibility) to suit an application. In some embodiments, the sheath 10 may be a relatively floppy component, while in other embodiments the sheath 10 may be relatively rigid. It is also contemplated that, in some embodiments, selected portions of the sheath 10 may be relatively rigid while other portions may be relatively flexible. The increased rigidity at the selected portions may be provided by incorporating different materials into the sheath 10 or by incorporating features (stiffening ribs, thicker regions, etc.) that impart rigidity to selected regions of the sheath 10. In some embodiments (such as, for example, when sheath 10 is relatively floppy), an instrument may be inserted into a lumen of the sheath 10 before the sheath 10 (along with the inserted instrument) is inserted into the body of the patient. In such an embodiment, the stiffness provided by the inserted instrument may guide the sheath 10 into the body. After the sheath 10 is appropriately positioned within the body, other instruments may be inserted through other lumens of the sheath 10. For example, in one exemplary embodiment, a reusable instrument may be inserted into the sealed first lumen 20 of a relatively floppy sheath 10 before the sheath 10 is inserted into a body cavity. Once the distal end 12 of the sheath 10 is appropriately positioned in the body, the disposable instruments may be inserted through the second and third lumens 22, 24. It is also contemplated that disposable instruments are also inserted into the sheath 10 before the sheath 10 is inserted into the body cavity.

In some embodiments, sheath 10 may be inserted into the body and positioned at a desired location in the body before the disposable and reusable instruments are inserted into the lumens of the sheath 10. In such an embodiment, the inserted sheath 10 acts as a guide to direct the instruments into the body. It is also contemplated that, in some embodiments, one or more instruments or guides may be inserted into the body, and the sheath 10 may be slid over the inserted instrument from the proximal end of the instrument. For example, in some exemplary applications, an instrument may first be inserted into the body (individually inserted or inserted through a guide tube, etc.). The proximal end of the inserted instrument (located outside the body) may be inserted into the distal end of the sheath (through an open lumen), and the sheath 10 pushed into the body until the distal end 12 is positioned at a desired location within the body. In such an embodiment, the inserted instrument may guide the sheath 10 to the desired location in the body. Once positioned at the desired location, the reusable instrument may then be inserted through the sealed first lumen 20.

Figure 1B:
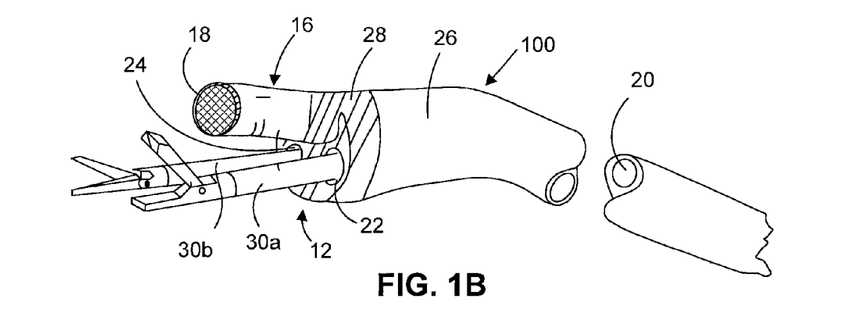
FIG. 1B is a schematic view of the distal end of an exemplary embodiment of a sheath of the current disclosure.
Figure 1C:
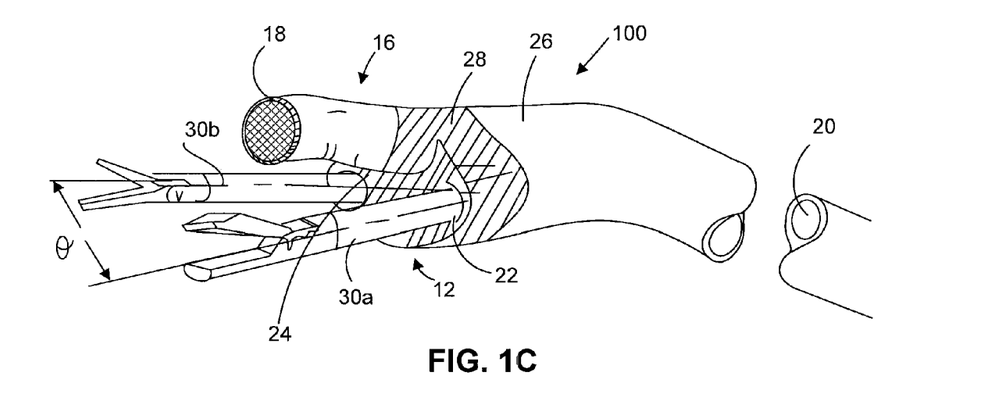
FIG. 1C is a schematic illustration of the distal end of the sheath of FIG. 1B post activation of the diverging element of the sheath.

In some embodiments, as illustrated in sheath 100 of FIGS. 1B and 1C, one or more diverging elements 28 may be included in the elongate body 26 to enable instruments 30a and 30b in the second and third lumens 22, 24 to diverge from each other at the distal end 12. FIG. 1B illustrates a view of sheath 100 before diverging element 28 is activated, and FIG. 1C illustrates a view of the sheath 100 after the activation of diverging element 28. These diverging elements 28 may include both active and passive devices. Activation of the diverging element 28 enables the ends of the instruments 30a, 30b that extend out of the second and third lumens 22, 24 to diverge from each other by any angle θ. Although FIGS. 1B and 1C illustrate the instruments 30a and 30b in the second and third lumens 22, 24 as diverging only from each other, in some embodiments, the diverging element 28 may also be configured to enable these instruments 30a, 30b to diverge from the distal end of the reusable instrument in the first lumen 20 also. Although the diverging element 28 may be positioned at any location in sheath 100, in some embodiments, the diverging element 28 may be positioned proximate the distal end 12 of the sheath 100 to enable the distal ends of the instruments delivered through sheath 100 to diverge from each other. The ability of the instruments that extend through sheath 100 to diverge from each other at the distal end may further assist the user in performing a medical procedure within the body.

Any feature that enables the instruments in the different lumens to diverge from each other may be used as diverging element 28. In some embodiments, the diverging element 28 may include a flexible section (such as a section made of a relatively more flexible material and/or having a smaller thickness) of elongate body 26 that can flex to enable the different instruments to separate from each other. In other embodiments, the diverging element 28 may include sections of the elongate body 26 having a variable flexibility. For instance, a section of the elongate body 26 proximate diverging element 28 may include balloons or cavities that may be selectively filled with air (or another fluid) to vary the flexibility in that region. As the balloons or cavities are filled, they also may enlarge, pushing the lumens 22, 24 away from one another if, for example, the balloon or cavity is between the lumens 22, 24. The balloons or cavities may be connected to a source of fluid located at the proximal end of the sheath 100, though a lumen extending through the sheath 100. In other embodiments, diverging element 28 may include sections of elongate body 26 in which the flexibility may be selectively varied thermally, electrically, or by another method. Diverging element 28 may involve shapes or geometries to promote divergence. In some embodiments, the diverging element 28 may create one or more ramps adjacent to a lumen to guide an instrument in the lumen in a particular direction. In some embodiments, the diverging element 28 may be bubble shaped, spherical or hemi-spherically shaped features to allow instruments to glance off the diverging element 28 and be diverted relative to another instrument. Although only one diverging element 28 is illustrated in FIGS. 1B and 1C, sheath 100 may include several diverging elements 28. In some embodiments, different diverging elements 28 may be associated with different lumens and may be positioned at different locations in sheath 100. The diverging element 28 may enable the distal ends of the instruments to diverge from each other and further assist in a medical procedure.

Figure 1D:
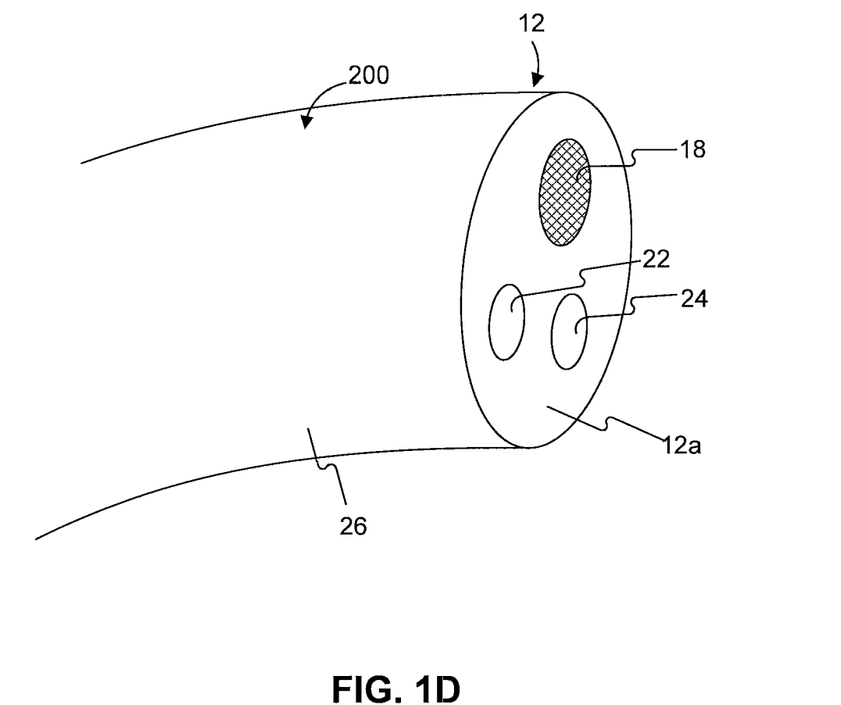
FIG. 1D is a schematic view of the distal end of another exemplary embodiment of a sheath of the current disclosure.

Although a protruding neck region 16 is illustrated in the sheaths 10 and 100 illustrated in FIGS. 1A, 1B, and 1C, in some embodiments, as illustrated in sheath 200 of FIG. 1D, the neck region 16 may be eliminated. In such embodiments, the first lumen 20 may terminate at the distal face 12a, and the viewing lens 18 may be provided at the distal face 12a. Although one sealed lumen (first lumen 20) and two open lumens (second lumen 22 and third lumen 24c) are illustrated in FIGS. 1A-1D, this is only exemplary. In general, any number of sealed and open lumens may be provided in sheath 200. Further, although these lumens are illustrated as being circular, in general, these lumens can have any cross-sectional shape. The cross-sectional shape may be fixed along the length or may vary along the length of elongate body 26. The change in cross-sectional shape along the length may be stepwise or continuous. In some embodiments, some or all lumens may be lined with a polymeric (or another) layer or coating (such as, for example, MDX coating, PTFE extrusions, etc.) to facilitate use. Further, the first, second, and third lumens 20, 22, 24 may be arranged in any pattern in sheath 200. In some embodiments, the first, second, and third lumens 20, 22, 24 may be arranged along a vertical axis as illustrated in sheath 10 of FIG. 1A or arranged in another pattern, such as, for example, positioned at the vertices of a triangle as illustrated in sheaths 100 and 200 of FIGS. 1B, 1C and 1D. It should be noted that the lumens extending through a sheath of the current disclosure may be arranged in any pattern, without limitation. The lumens may be of any size. In some embodiments, the lumens may be sized to fit most commonly used tools therethrough. In some embodiments, one or more of the lumens may be sized for a desired tool.

Figure 1E:
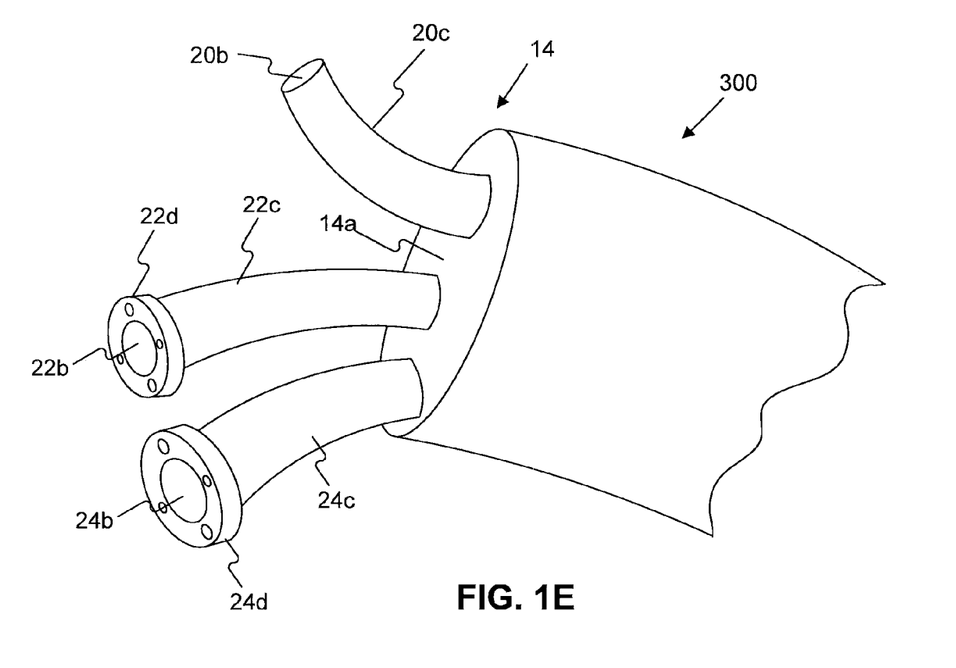
FIG. 1E is a schematic view of the proximal end of an exemplary embodiment of a sheath of the current disclosure.
Figure 1F:
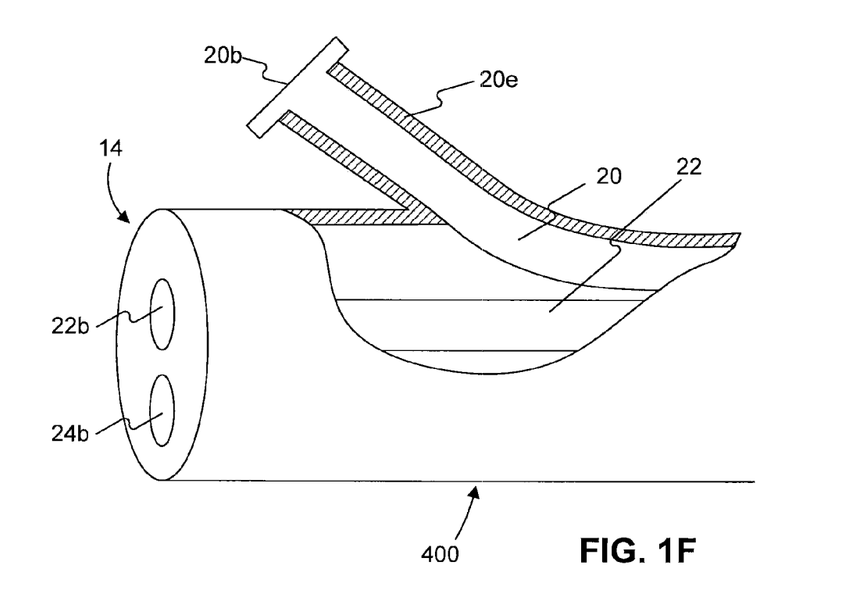
FIG. 1F is a schematic view of the proximal end of another exemplary embodiment of a sheath of the current disclosure.

Although in FIG. 1A, the proximal ends of the first, second, and third lumens 20, 22, 24 are illustrated as terminating (at openings 20b, 22b, and 24b, respectively) on proximal face 14a, this is only exemplary. In some embodiments, as illustrated in sheath 300 of FIG. 1E, one or more of these lumens may include projecting portions (such as, for example, 20c, 22c, and 24c) that project past the proximal face 14a. The projecting portions may be flexible or rigid (or combinations thereof) and some or all of these projecting portions may include seals (such as, for example, seals 22d and 24d on projecting portions 22c and 24c respectively) or other fixtures. In some embodiments, these projecting portions of the lumens may mate with other equipment that may assist in the medical procedure. For example, in an exemplary medical procedure, second lumen 22 may be an irrigation lumen configured to facilitate fluid flow to a work site within the body, and the third lumen 24 may be an aspiration lumen configured to provide suction to the work site. In such an embodiment, the projecting portion 22c of the second lumen 22 may be attached to a fluid tank (or another source of fluid), and the projecting portion 24c of the third lumen 24 may be attached to a suction/irrigation pump (or another device that provides suction). The seals 22d and 24d may assist in providing a fluid tight connection between the fluid source/suction pump and the corresponding lumen. In some such embodiments, the distal ends of the second and third lumens 22, 24 may also include devices that may assist in its functioning. For example, a nozzle (or another similar device configured to alter fluid flow) may be attached to the distal end 12 of second lumen 22 to assist in controlling the fluid at a desired location. Fluid may be directed to the work site through the second lumen 22 and suction may be provided through the third lumen 24 to remove the fluid (and/or biological material) from the work site. In this manner, a tissue sample may be extracted out of the body through the third lumen 24. In other embodiments (such as, for example in sheath 400 of FIG. 1F), a port 20e positioned between the proximal and distal ends 14 and 12 of the sheath 400 may provide access to the first lumen 20a. In some embodiments, as illustrated in FIG. 1F, port 20 may extend at an angle from the surface of the elongate body 26.

Any type of medical instrument known in the art may be provided through the second and the third lumens 22, 24. These medical instruments may be configured to perform specific tasks to assist in the desired medical procedure. The medial instruments may include (but not limited to) graspers, forceps, needles, hooks, dissectors, etc. In some cases, an end effector that is configured to perform the task may be coupled to an elongate member that extends into the body through the second and the third lumens 22, 24. The elongate member may operatively couple the end effector to an actuation device at the proximal end 14 to operate the end effector. Since the distal ends of the second and third lumens 22, 24 are open, the medical instruments directed into the body through these lumens may directly contact body tissue. Therefore, in some exemplary medical procedures using a disclosed sheath, these medical instruments may be sterilized and reused, or may be disposed (along with the sheath) after use.

Figure 2A:
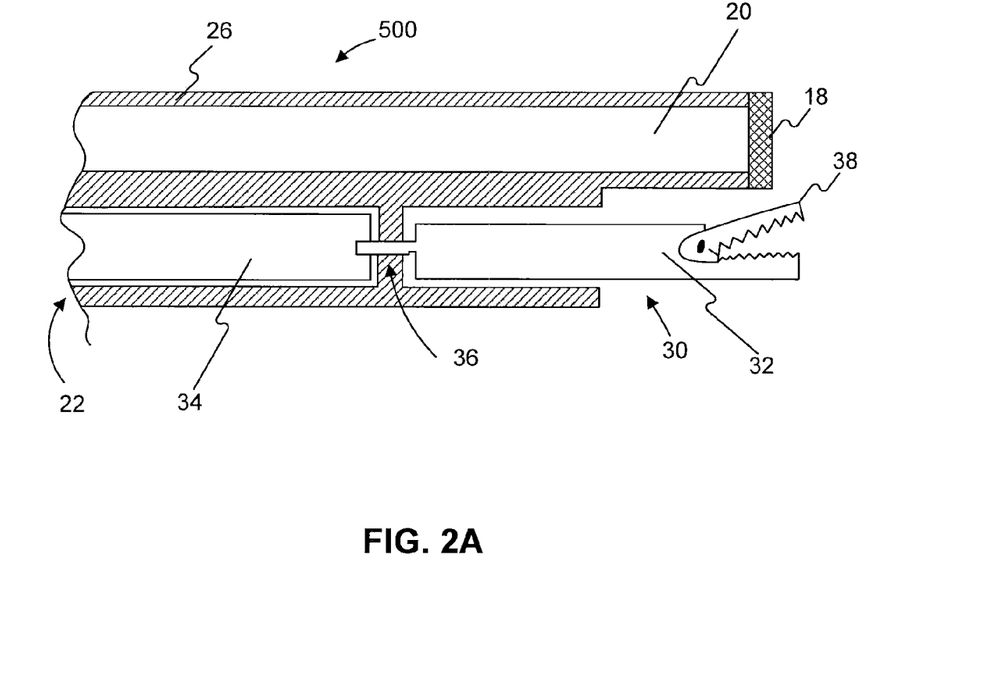
FIG. 2A is a schematic view of an exemplary embodiment of a sheath with a medical instrument having disposable and reusable portions.

In some embodiments of a sheath, a medical instrument directed through the second or third lumen 22, 24 may be only partially disposable with a remainder of the instrument being reusable. In these embodiments, a portion of the instrument that contacts body tissue may engage with a reusable portion 34 of the instrument that is positioned within the sheath and isolated from body tissue. FIG. 2A illustrates one exemplary embodiment of sheath 500 having a disposable portion 32 preloaded to the distal end 12 thereof. The disposable portion 32 may include an end effector 38 at its distal end, and may mate with a reusable portion 34 that extends through the second lumen 22 of the sheath 500. The disposable and reusable portions 32, 34 together form the instrument 30. The reusable portion 34 may join with the disposable portion 32 at an interface 36 within the sheath 500. The interface 36 may include features configured to transmit relative motion and/or signals between the coupled reusable and disposable portions 34, 32 to enable the end effector 38 (at the distal end of the disposable portion 32) to be controlled by an actuation device at the proximal end of the reusable portion 34. The interface 36 may also be configured to prevent biological tissue from contacting the reusable portion 34 within the sheath 500. In some embodiments, the interface 36 may also be configured to prevent or minimize biological fluids from entering the sealed portion of the second lumen 22 that contains the reusable portion 34 of instrument 30. In some embodiments, a disposable portion 32 of an instrument may pierce through a wall of the sheath 500

Figure 2B:
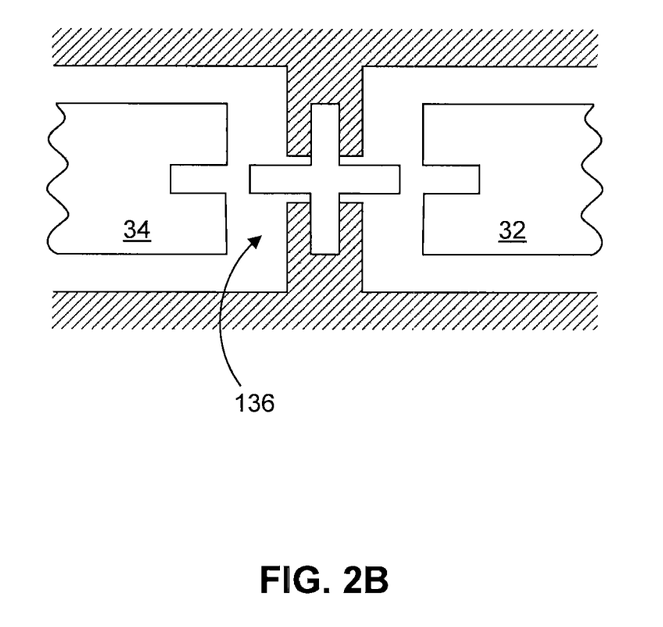
FIG. 2B is a schematic view of an exemplary embodiment of the interface between the disposable and reusable portions of the medical instrument of FIG. 2A.

Any type of interface that enables the disposable and reusable portions 32, 34 to be coupled together while isolating the reusable portion 34 from body tissue may be used as interface 36. Interface 36 may be an integral part of one of the portions (such as, for example, an integral part of the disposable portion 32 as illustrated in FIG. 2A), or may be a part of the sheath 500. FIG. 2B illustrates an exemplary interface 136 that is part of the sheath. In such an embodiment, the disposable and reusable portions 32, 34 of the instrument 30 may be separately coupled to the interface 136. In an embodiment using an instrument 30 with disposable and reusable portions 32, 34, the sheath 500 along with the disposable portion 32 may be disposed after use while the reusable portion 34 may be reused. In general, any portion of an instrument can be the reusable portion 34. For instance, in some embodiments, only a portion of the end effector 38 may be disposable while the remaining portions of the instrument 30 may be reusable. In other embodiments, only a portion of the actuation device may be reusable while the remaining portions of the instrument 30 may be disposable.

In some exemplary medical procedures using an instrument 30 with disposable and reusable portions 32, 34, the two portions may be first coupled together before the sheath 500 is inserted into the body. In other embodiments, only one of the portions (such as for example, the disposable portion 32) may be coupled to the sheath 500 before the sheath 500 is inserted into to the body. The remaining portion (such as, for example, the reusable portion 34) may be coupled after the sheath 500 is inserted into to the body.

Figure 3A:
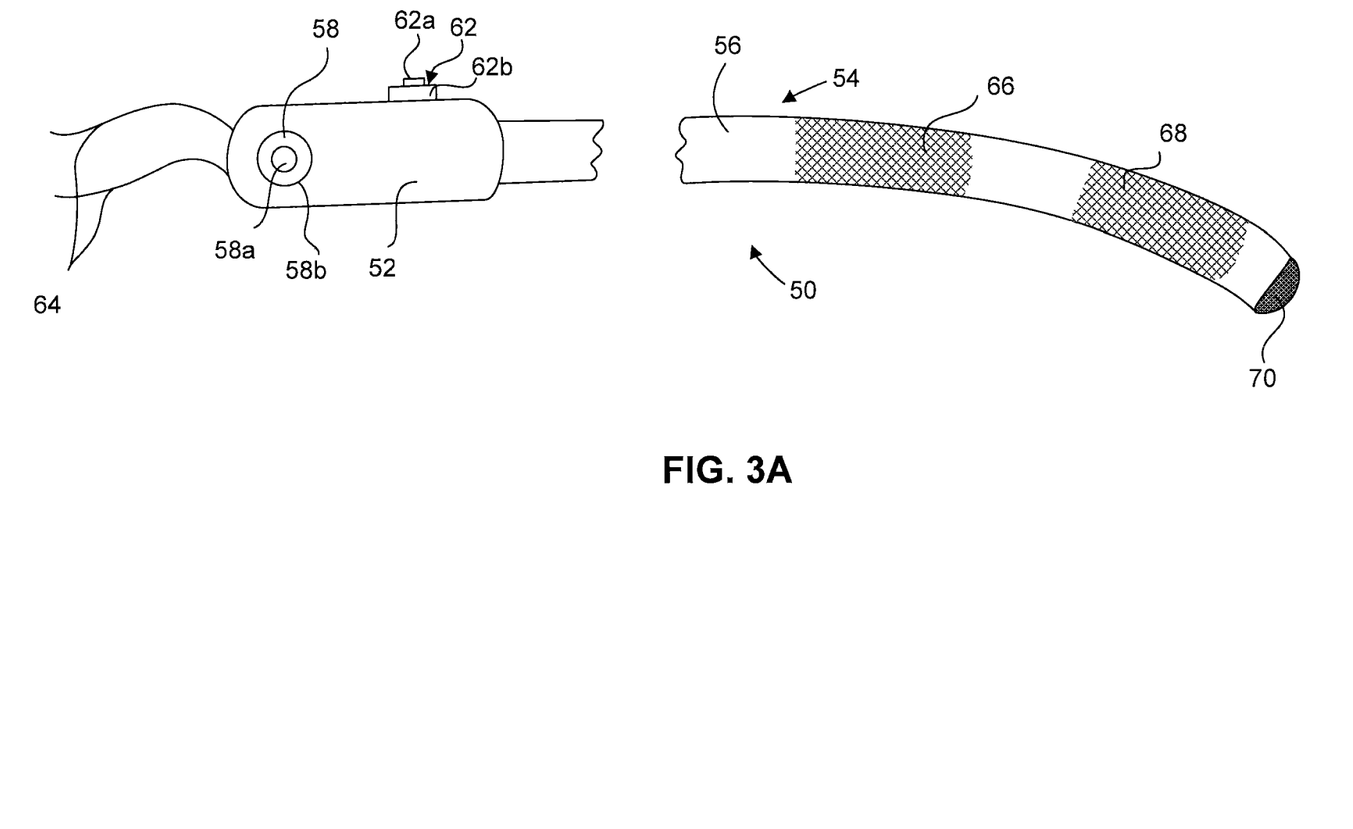
FIG. 3A is a schematic view of an exemplary reusable medical instrument that may be used with a sheath of the current disclosure.

FIG. 3A illustrates a reusable instrument 50 that may directed into the body though a sealed first lumen 20 of a disclosed sheath (for example, sheath 10 of FIG. 1A). Any instrument (such as, for example, a light wand, an imaging device, an endoscope, etc.) may serve as the reusable instrument 50. The reusable instrument 50 may include a flexible elongate section 56 extending from a handle 52. The handle 52 may include controls 58, 62 that may activate different features of the reusable instrument 50. The elongate section 56 may include one or more bendable sections, such as, for example, a first bendable section 66 and a second bendable section 68, positioned along its length. In some embodiments, these bendable sections 66, 68 may be configured to bend or deflect in response to the actuation of the controls 58, 62. In some embodiments, one of these controls (such as, for example, control 58) may actuate the first bendable section 66 and the other control (such as, for example, 62) may actuate the second bendable section 68. Other embodiments of reusable instruments may be controlled in a different manner. For example, in some embodiments, control 58a may be actuated to deflect the first bendable section 66 along a horizontal axis (that is, left/right) and control 58b may be actuated to deflect the second bendable section 68 along a horizontal axis. Similarly, controls 62a and 62b may actuate the first and second bendable sections 66, 68, respectively, along a vertical axis (up/down). These controls may actuate the bendable sections in any manner. In some embodiments, these controls may, mechanically, thermally, or electrically actuate the bendable sections to deflect in a desired direction. For example, use of shape memory materials or electroactive may assist in deflecting the sheath in a desired direction. In other embodiments, the bendable sections may incorporate features (such as a fluid cavity, etc.) or devices (such as, actuators) that assist in the deflection of the elongate section 56 in a desired direction. Cables 64 (or conduits) may direct signals (and/or fluids) to the reusable instrument 50 to assist in the deflection of the bendable sections. In some embodiments, the cables 64 may be operated mechanically, thermally, or electrically.

The distal-most end of elongate section 56 may include an optical element 70 that may receive and/or transmit light. Any device (such as, a light source, imaging device, etc.) that may emit light and/or may operate using received light may serve as the optical element 70. For example, optical element 70 may include a camera, imaging sensor (such as, for example, a complimentary metal-oxide semiconductor or a CMOS sensor), or another image receiving device (such as, for example, a fiber optic imaging device). Optical element 70 may transmit an image signal to a monitor or other display device positioned outside the body and viewable by the user of the device. The image signals may correspond to still pictures and/or transient images that display time varying images of the work site within the body. In some embodiments, optical element 70 may transmit the image signals wirelessly, while in other embodiments, wires or cables embedded in the reusable instrument 50 may be used to transit these image signals. It is also contemplated that, in some embodiments, control signals may also be transmitted to the optical element 70 from outside the body, wirelessly or through the cables embedded in the reusable instrument 50. Additionally or alternatively, optical element 70 may also include an illumination device that is configured to illuminate the work site. The illumination device may include, among others, bulbs, LEDs, fiber optic cables and light guides. In some embodiments, the second bendable section 68 may be positioned proximate the optical element 70 and the first bendable section 66 may be positioned proximal to the second bendable section 68.

Figure 3B:
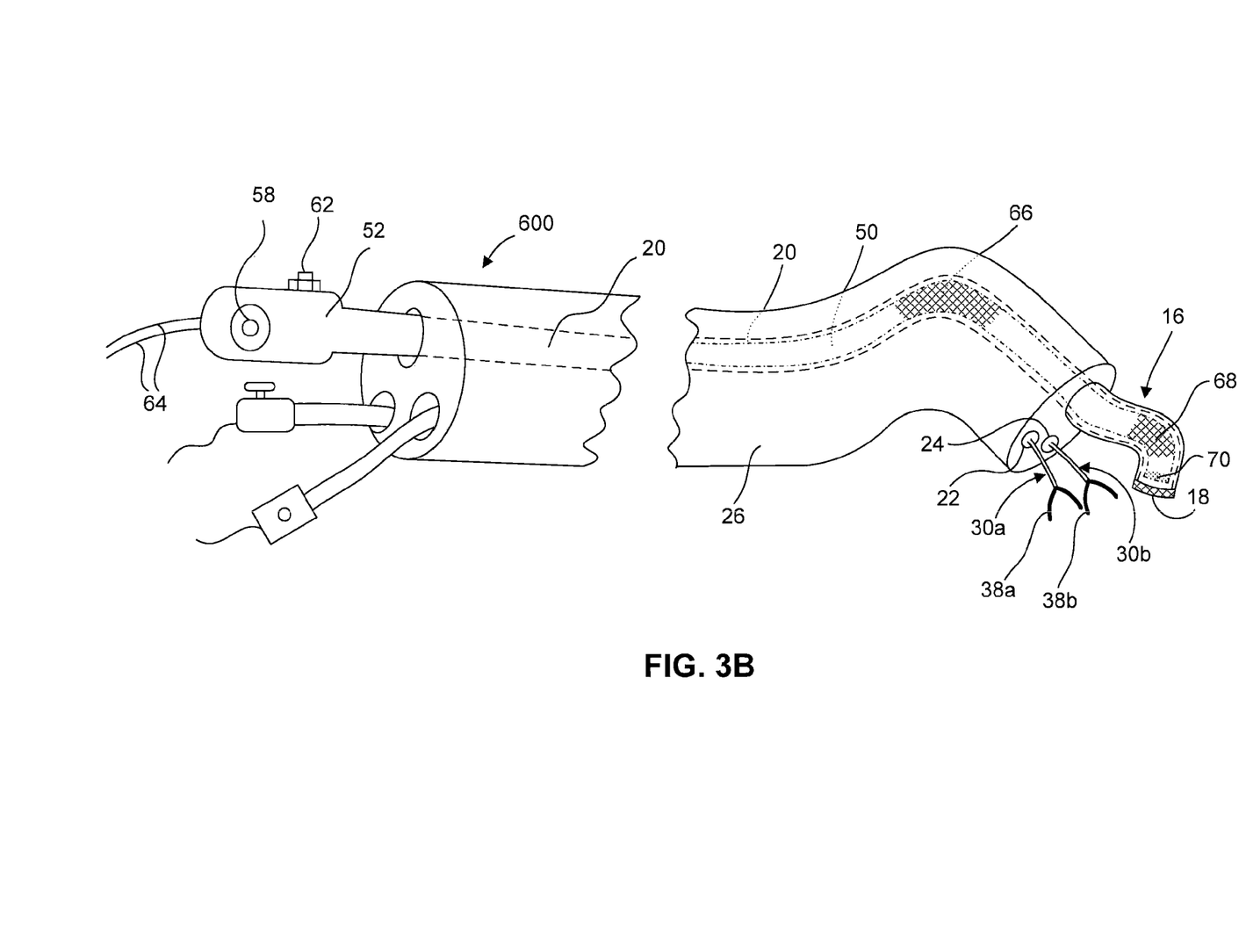
FIG. 3B is a schematic illustration of the reusable medical instrument of FIG. 3A used with an embodiment of a sheath of the current disclosure.

FIG. 3B illustrates an embodiment of sheath 600 with a reusable instrument 50 extending through a first lumen 20 and two disposable instruments 30a, 30b extending through the second and third lumens 22, 24, respectively. The reusable instrument 50 may be extended through the first lumen 20 to position the optical element 70 proximate the viewing lens 18. When the reusable instrument 50 is thus positioned, in some embodiments, the second bendable section 68 of the reusable instrument 50 may be positioned in the neck region 16 of the sheath 600. In this configuration, actuating the second bendable section 68 to deflect this region of the reusable instrument 50 may be used to position the viewing lens 18 and the optical element 70 in any manner suited to view and/or illuminate the work site (such as, for example, in an orientation suited to obtain a bird's eye view of the work site). Actuating the second bendable section 68 may also be used to guide or steer the sheath 600 and the instruments 30a, 30b extending through the second and third lumens 22, 24 to the work site. Actuating the first bendable section 66 may also be used to guide and position the distal end 12 of the sheath 600 in a desirable manner within the body. Used together, the first and second bendable sections 66, 68 may be used to position the sheath 600, and the instruments therein, in a desirable manner within the body. For example, the first bendable section 66 may be actuated to raise the distal end 12 of sheath 600 off the patient's anatomy and the second bendable section 68 may be actuated to steer and direct the instruments to a desired location and position the optics in a manner most suited to visualize and/or illuminate the work site. Thus, a sheath of the current disclosure may be used to attach an optics lumen to a standard flexible disposable instrument. The sheath may also be used to provide steering capability to a standard non-articulating instrument by the use of a steerable instrument (such as, for example, an endoscope) in the sheath.

Sheath 10 (see FIG. 1A) may be affixed to an instrument (reusable instrument 50 or disposable instrument 30) in any manner. In some embodiments, an instrument may be slid into (or squeezed into) a lumen of the sheath 10, while in other embodiments, the sheath 10 may be slid over the instrument. It is also contemplated that the sheath may be rolled over an instrument (similar to a condom), wrapped, zip-locked, hook and looped (such as, by using a Velcro® like attachment mechanism), adhered or expanded on the instrument. Expanding the sheath 10 on an instrument may include reversibly expanding the sheath 10 (by, for example, inflating with air or another fluid, by using temperature or a chemical change to increase or decrease the size of a lumen, etc.) to insert an instrument through the lumen and then contracting the lumen.

The sheath may be attached to an instrument in any manner and any order without limitation. For example, in some exemplary medical procedures, all the instruments (reusable instrument 50 and disposable instrument 30a, 30b, etc.) may be first inserted into the sheath 10 (or attached to the sheath by using another one of the procedures described above) before the sheath 10 (along with the inserted instruments) is inserted into the body of the patient. In other embodiments, only some of the instruments may be inserted into the sheath 10 before the sheath 10 is inserted into the body. The other instruments may be inserted into the sheath 10 after the sheath 10 is within the body. For example, a reusable medical instrument 50 may first be inserted into the sheath 10 before the sheath 10 is inserted into the body of the patient. Disposable instruments 30a, 30b, etc. may be inserted into the second and third lumens 22, 24 of the sheath 10 after the sheath is in the body. It is also contemplated that, in some exemplary medical procedures, one or more instruments may be first inserted into the body before the sheath is slid over these instruments. Other instruments may then be inserted through the lumens of the sheath. It is also contemplated that, in some embodiments, the sheath 10 may be first inserted into the body before the instruments are inserted into their respective lumens.

Figure 4:
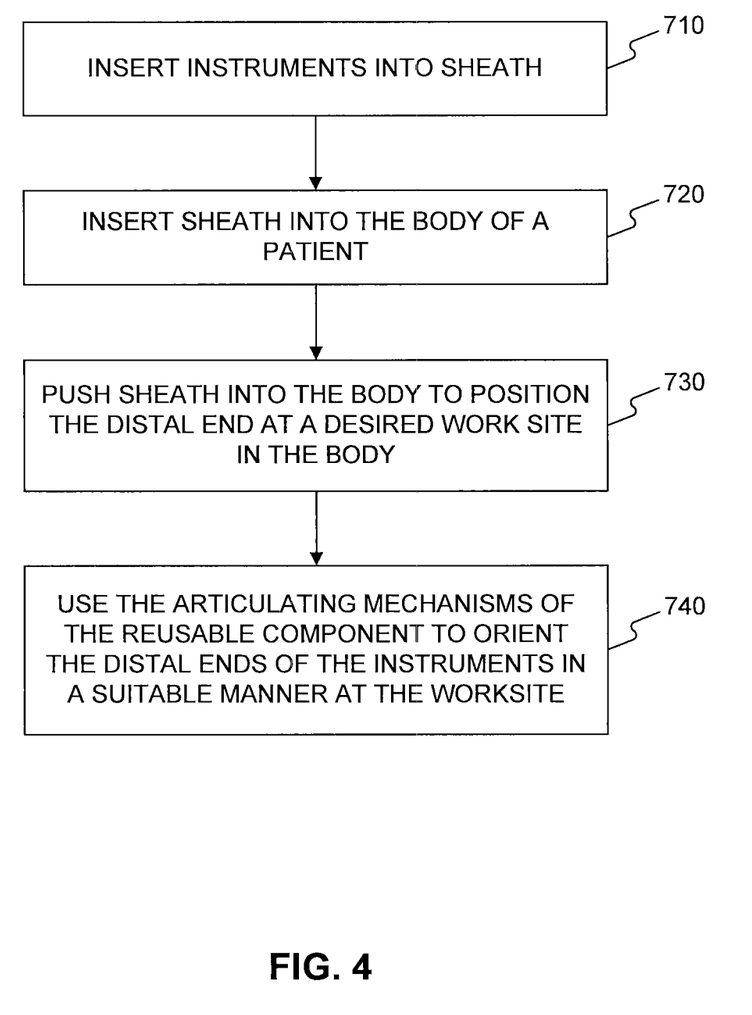
FIG. 4 is a flow chart illustrating an exemplary medical procedure using a sheath of the current disclosure.

FIG. 4 is a flow chart that illustrates an exemplary method of using a sheath of the current disclosure. As illustrated in FIG. 4, a reusable instrument 50 may be inserted into a closed lumen 20 and one or more disposable medical instruments (30a, 30b, etc.) may be inserted into one or more open lumens 22, 24 of the sheath 10 (step 710). Although these instruments are described as being inserted into the sheath, as discussed above, these instruments may be attached in any manner to sheath 10. The sheath 10, along with the instruments, therein may then be inserted into the body of a patient (step 720). The sheath 10 may be inserted into the body through a natural anatomic opening or through an incision on the body of the patient. The sheath 10 may be pushed into the body to a work site within the body (step 730). The articulating mechanisms (such as, the first and/or second bendable sections 66, 68) of the reusable instrument 50 may be activated to steer and guide the sheath through the body and position the distal end 12 of the sheath 10, the viewing lens 18, and the end effectors 38a, 38b in a desired configuration at the work site (step 740). In some embodiments, the neck region 16 of the first lumen 20 may be manipulated to position the viewing lens 18 over the work site to get a bird's eye view of the work site. Although in the description above, the instruments are described as being inserted into the sheath 10 before the sheath 10 is inserted into the body, as described previously, this is only exemplary and in other embodiments, sheath 10 (alone or with some instruments inserted therein) may be inserted into the body before the instruments are inserted into the sheath 10.

The embodiments described herein are exemplary only, and it will be apparent to those skilled in the art that various modifications and variations can be made in the disclosed systems and processes without departing from the scope of the invention. Other embodiments of the invention will be apparent to those skilled in the art from consideration of the specification and practice of the invention disclosed herein. It is intended that the specification and examples be considered as exemplary only, with a true scope of the invention being indicated by the following claims.

What is claimed is:

1. A sheath for a medical instrument, comprising:
    an elongate body extending from a proximal end to a distal face, the elongate body comprising a diverging element proximate the distal face;
    a neck region extending from the distal face;
    a first hollow lumen extending from a first end proximate the proximal end to a second end distal the distal face;
    a second lumen extending from proximate the proximal end to the distal face;
    a third lumen extending from the proximal end to the distal face; and
    a transparent window positioned at the second end of the first lumen to seal the first lumen at the second end, the transparent window being configured to transmit light therethrough;
    wherein each of the second lumen and the third lumen comprises a distal-most portion open at the distal face;
    wherein the distal face includes a single continuous surface defining an opening of the distal-most portion of the second lumen and an opening of the distal-most portion of the third lumen; and
    wherein the diverging element is configured to change an orientation of the openings of the second and the third lumens relative to each other upon activation of the diverging element.

2. The sheath of claim 1, further including a sealing device coupled to the second lumen proximate the proximal end and configured to seal around a medical instrument inserted through the sealing device.

3. The sheath of claim 1, wherein the diverging element is disposed between the second lumen and the third lumen.

4. The sheath of claim 1, wherein activation of the diverging element causes the distal-most portions of the second lumen and the third lumen to diverge from each other.

5. The sheath of claim 4, wherein activation of the diverging element changes an orientation of the distal-most portion of at least one of the second lumen or the third lumen relative to a distal portion of the first hollow lumen.

6. The sheath of claim 1, wherein the first lumen is open at the first end.

7. The sheath of claim 1, wherein the neck region includes the first lumen, the neck region extending from the distal face to the second end of the first lumen.

8. The sheath of claim 7, wherein the neck region is configured to deflect relative to the distal face of the elongate body.

9. The sheath of claim 1, wherein the sheath further includes a port that extends from a location proximate the proximal end to the first end, at least a portion of the first lumen being positioned in the port.

10. The sheath of claim 1, wherein the transparent window seals the first lumen such that entry of fluids into the first lumen at the second end is substantially prevented.

11. The sheath of claim 1, wherein the first hollow lumen comprises one or more bendable sections.

12. The sheath of claim 1, wherein the transparent window is planar.

13. The sheath of claim 1, wherein the neck region defines exactly one lumen, a distal portion of the first hollow lumen being the exactly one lumen defined by the neck region.

14. The sheath of claim 1, wherein the neck region is fixed at the distal face.

15. The sheath of claim 1, wherein the diverging element is flexible.

16. The sheath of claim 1, wherein the diverging element includes a cavity in communication with a source of fluid.

17. A sheath for a medical instrument, comprising:
    an elongate body extending from a proximal end to a distal face, the elongate body comprising a flexible diverging element proximate the distal face;
    a neck region extending from the distal face;

a first hollow lumen extending from a first end proximate the proximal end to a second end distal the distal face;

a second lumen extending from the proximal end to the distal face; and a third lumen extending from the proximal end to the distal face;

wherein each of the second lumen and the third lumen comprises a distal-most portion open at the distal face;

wherein the distal face includes a single continuous surface defining an opening of the distal-most portion of the second lumen and an opening of the distal-most portion of the third lumen; and wherein the diverging element is configured to change an orientation of the openings of the second and the third lumens relative to each other such that they diverge from each other upon activation of the diverging element.

18. The sheath of claim 17, wherein the neck region is fixed at the distal face and defines exactly one lumen, and wherein a distal portion of the first hollow lumen is the exactly one lumen defined by the neck region.

19. A sheath for a medical instrument, comprising:

an elongate body extending from a proximal end to a distal face, the elongate body comprising a diverging element enclosed within the elongate body and located entirely proximal to the distal face;

a neck region extending from the distal face, a proximal end of the neck region being fixed at the distal face, and the neck region defining exactly one lumen;

a first hollow lumen extending from a first end proximate the proximal end to a second end distal the distal face, the first hollow lumen including a transparent window at the second end, a distal portion of the first hollow lumen being the exactly one lumen defined by the neck region;

a second lumen extending from the proximal end to the distal face; and a third lumen extending from the proximal end to the distal face;

wherein each of the second lumen and the third lumen comprises a distal-most portion open at the distal face; and wherein the diverging element is configured to change an orientation of the distal-most portions of the second and the third lumens relative to each other upon activation of the diverging element.

20. The sheath of claim 19, wherein the diverging element includes a cavity in communication with a source of fluid.

* * * * *